United States Patent
Bourque et al.

(10) Patent No.: US 9,662,125 B2
(45) Date of Patent: May 30, 2017

(54) RETRODRILL SYSTEM

(71) Applicant: Smith & Nephew, Inc., Memphis, TN (US)

(72) Inventors: Bernard J. Bourque, Taunton, MA (US); Michael C. Ferragamo, Foster, RI (US); Ben K. Graf, Madison, WI (US); William Davis, Hingham, MA (US)

(73) Assignee: Smith & Nephew, Inc., Memphis, TN (US)

( * ) Notice: Subject to any disclaimer, the term of this patent is extended or adjusted under 35 U.S.C. 154(b) by 290 days.

(21) Appl. No.: 14/503,792

(22) Filed: Oct. 1, 2014

(65) Prior Publication Data

US 2015/0018831 A1 Jan. 15, 2015

Related U.S. Application Data

(62) Division of application No. 13/752,713, filed on Jan. 29, 2013, now Pat. No. 8,882,773, which is a division (Continued)

(51) Int. Cl.
| | | |
|---|---|---|
| *A61B 17/16* | (2006.01) | |
| *A61B 17/17* | (2006.01) | |
| *A61B 17/88* | (2006.01) | |

(52) U.S. Cl.
CPC ...... *A61B 17/1675* (2013.01); *A61B 17/1617* (2013.01); *A61B 17/17* (2013.01);

(Continued)

(58) Field of Classification Search
CPC ............ A61B 17/1675; A61B 17/1617; A61B 17/1764

(Continued)

(56) References Cited

U.S. PATENT DOCUMENTS

| 4,298,074 A | 11/1981 | Mattchen |
| 7,044,863 B1 * | 5/2006 | Brewster ............ A63B 37/0002 |
| | | 473/129 |

(Continued)

FOREIGN PATENT DOCUMENTS

| JP | S5628308 | 3/1981 |
| JP | 05184521 | 7/1993 |

(Continued)

OTHER PUBLICATIONS

Office Action in corresponding Japanese Application No. 2013-188051 mailed Jul. 28, 2014.

(Continued)

*Primary Examiner* — Christopher Beccia
(74) *Attorney, Agent, or Firm* — Burns & Levinson LLP; Joseph M. Maraia

(57) ABSTRACT

The present disclosure relates to a method of creating a bone tunnel during ligament reconstruction surgery. The method includes placing a guide wire through the femur, the guide wire having a first end portion including a pointed tip and a second end portion; placing a drill mechanism over the first end portion of the guide wire, the drill mechanism having a first end portion including a drill bit and a second end portion including an attachment portion; coupling an adaptor assembly to the attachment portion, the adaptor assembly including a shaft; coupling a drill to the shaft and operating the drill to create a tunnel in the femur; coupling a drill bit assembly to the second end portion of the guide wire and locating the assembly against the drill bit of the attachment portion; and operating the drill to create a counter bore within the tunnel.

8 Claims, 14 Drawing Sheets

Related U.S. Application Data of application No. 12/399,397, filed on Mar. 6, 2009, now Pat. No. 8,388,621.

(60) Provisional application No. 61/034,189, filed on Mar. 6, 2008.

(52) U.S. Cl.
CPC ...... *A61B 17/1714* (2013.01); *A61B 17/1764* (2013.01); *A61B 17/8897* (2013.01)

(58) Field of Classification Search
USPC .......................................................... 606/80
See application file for complete search history.

(56) References Cited

U.S. PATENT DOCUMENTS

| | | | | |
|---|---|---|---|---|
| 2004/0199166 A1* | 10/2004 | Schmieding | ....... | A61B 17/1617 606/79 |
| 2004/0267266 A1 | 12/2004 | Daniels et al. | | |
| 2008/0195101 A1* | 8/2008 | Lechot | ............... | A61B 17/1617 606/79 |

FOREIGN PATENT DOCUMENTS

| JP | 10118084 | 12/1998 |
|---|---|---|
| JP | 11500947 | 1/1999 |
| JP | 2001021251 | 1/2001 |
| JP | 2004513739 | 5/2004 |
| JP | 2005527312 | 9/2005 |
| JP | 2007061154 | 3/2007 |

OTHER PUBLICATIONS

Patent Examination Report No. 1 in corresponding Australian Patent Application mailed May 2, 2013.

Office Action in corresponding Japanese Application No. 2010-549905 mailed Jun. 11, 2013.

* cited by examiner

RETRODRILL SYSTEM

CROSS-REFERENCE TO RELATED APPLICATIONS

This application is a divisional application of co-pending U.S. patent application Ser. No. 13/752,713, entitled "RETRODRILL SYSTEM," filed Jan. 29, 2013, which is a divisional application U.S. patent application Ser. No. 12/399,397, now issued U.S. Pat. No. 8,388,621, entitled "RETRODRILL SYSTEM," filed Mar. 6, 2009, which claims the benefit of U.S. Provisional Patent Application Ser. No. 61/034,189, filed Mar. 6, 2008, the disclosures of which are incorporated by reference in their entirety.

BACKGROUND

1. Field of Technology

The present disclosure relates to the creation of bone tunnels during ligament reconstruction surgery, and more specifically, the creation of femoral bone tunnels.

2. Related Art

For torn knee ligament reconstruction, there has been an evolution in the anatomic femoral placement of the tissue graft. This can be accomplished by several methods all of which provide the ability to create a tunnel socket from the inside to the outside of the femur. Without hyperflexing the knee, a curved drilling path is needed to accomplish this procedure. A curved guide wire is first placed through the femur to act as a guide pin. An appropriate sized reamer is then advanced over the guide wire to create a drilled bone tunnel. A shortcoming of one of the present methods is the size of the reamer. The flexible reamers that are currently produced can't easily be made smaller than 7 mm. The size of the bone tunnel is important for proper placement of the tissue graft and for maintaining the tissue graft within the tunnel.

SUMMARY

In one aspect, the present disclosure relates to a method of creating a bone tunnel during ligament reconstruction surgery. The method includes placing a guide wire through a femur, the guide wire having a first end portion including a pointed tip and a second end portion; placing a drill mechanism over the first end portion of the guide wire, the drill mechanism having a first end portion including a drill bit and a second end portion including an attachment portion; coupling an adaptor assembly to the attachment portion, the adaptor assembly including a shaft; coupling a drill to the shaft and operating the drill to create a tunnel in the femur; coupling a drill bit assembly to the second end portion of the guide wire and locating the drill bit assembly against the drill bit of the attachment portion; and operating the drill to create a counter bore within the tunnel.

In another aspect, the present disclosure relates to a drill mechanism. The drill mechanism includes a first end portion including a drill bit; and a second end portion including an attachment portion, the attachment portion including a first set of slots positioned on opposite sides of the portion and extending parallel with a longitudinal axis of the mechanism, the first set of slots including a first end and a second end, and a second set of slots located at the second end of the first set of slots, the second set of slots extending perpendicular to the first set of slots.

In yet another aspect, the present disclosure relates to an adaptor assembly for a drill mechanism. The adaptor assembly includes an adaptor including a housing and a shaft coupled to the housing, the housing including a wall, a first pin disposed through the wall, and a second pin disposed through the wall opposite the first pin; a ring disposed within the shaft; a collar coupled to the shaft; and a nut coupled to the housing of the adaptor, the nut including an opening through which the shaft is disposed. In an embodiment, the adaptor assembly further includes a drill mechanism disposed within the housing of the adaptor, the drill mechanism including an attachment portion including a set of slots, the drill mechanism disposed within the housing such that the first pin and the second pin are housed within the set of slots.

In a further aspect, the present disclosure relates to drill bit assembly. The drill bit assembly includes a housing; a knob coupled to the housing; and a locking mechanism disposed within a cavity of the housing, the locking mechanism comprising a shaft, a first finger coupled to the shaft, a second finger coupled to the shaft, and a detent located between the first finger and the second finger, wherein the locking mechanism is movable within the cavity.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

BRIEF DESCRIPTION OF THE DRAWINGS

The accompanying drawings, which are incorporated in and form a part of the specification, illustrate the embodiments of the present disclosure and together with the written description serve to explain the principles, characteristics, and features of the disclosure. In the drawings:

FIG. 2A shows the first end portion of the guide wire of FIG. 2.

FIG. 4A shows the attachment portion of the drill mechanism of the present disclosure.

DETAILED DESCRIPTION OF THE EMBODIMENTS

The following description of the preferred embodiment(s) is merely exemplary in nature and is in no way intended to limit the disclosure, its application, or uses.

Figure 1:
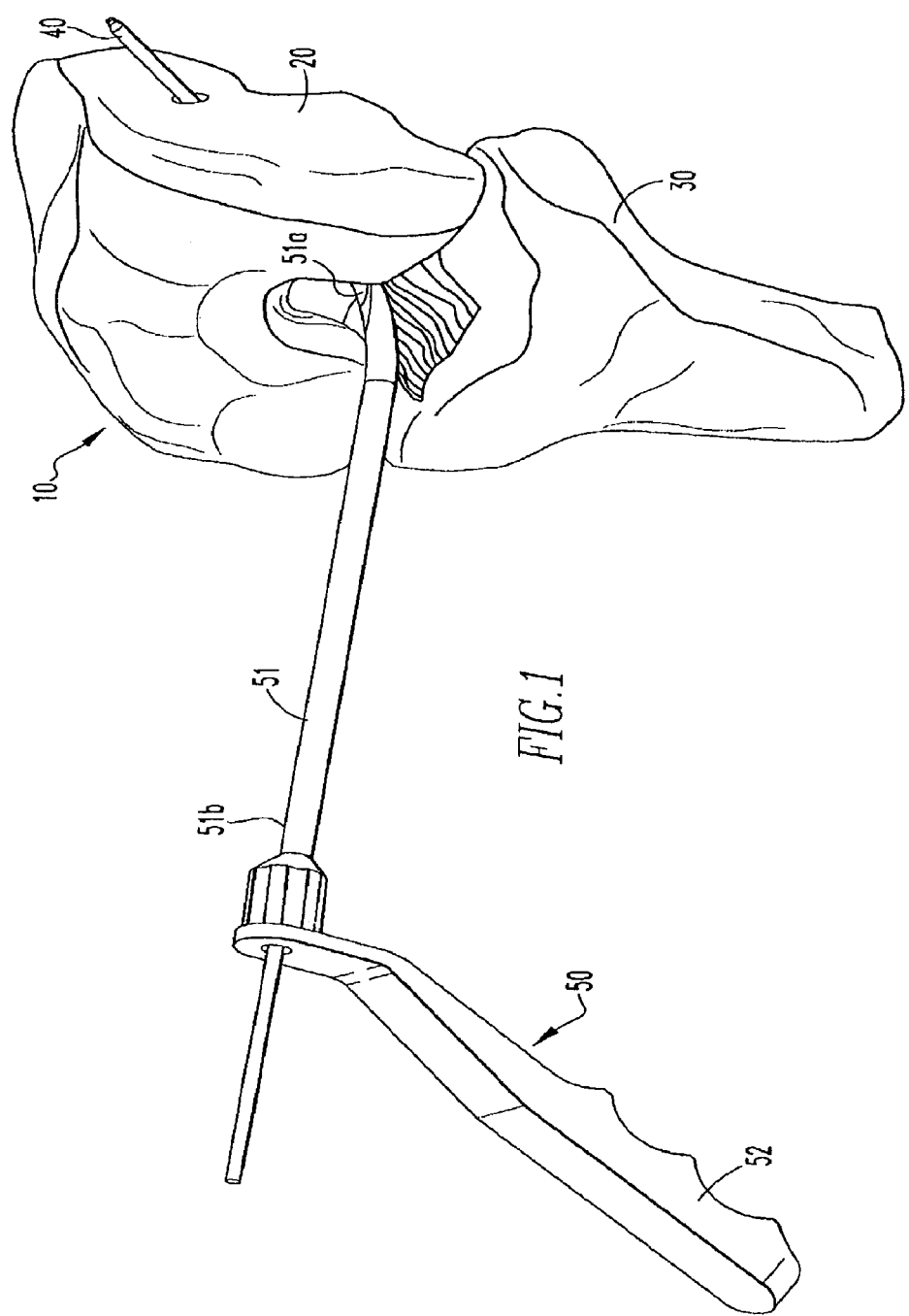
FIG. 1 shows placement of a guide wire of the present disclosure through a femur.

FIG. 1 shows a knee joint 10 including a femur 20 and a tibia 30, and specifically, insertion of a guide wire 40 into the femur 20 via use of a drill guide 50 and a drill (not shown). The guide wire 40 will be used, in combination with the drill, to drill a tunnel into the femur 20 in preparation for receipt of a tissue graft, as will be further described below. Prior to inserting the guide wire 40 into the femur 20, the surgeon views the femur 20 arthroscopically and determines the best location for inserting the guide wire 40. Subsequently, the surgeon inserts a cannulated shaft 51 of the guide 50 into the joint 10 and positions a distal end 51a of the shaft 51 against the femur 20. The shaft 51 includes the distal end 51a and a proximal end 51b. The distal end 51a is curved and the proximal end 51b is coupled to a handle 52.

Figure 2:
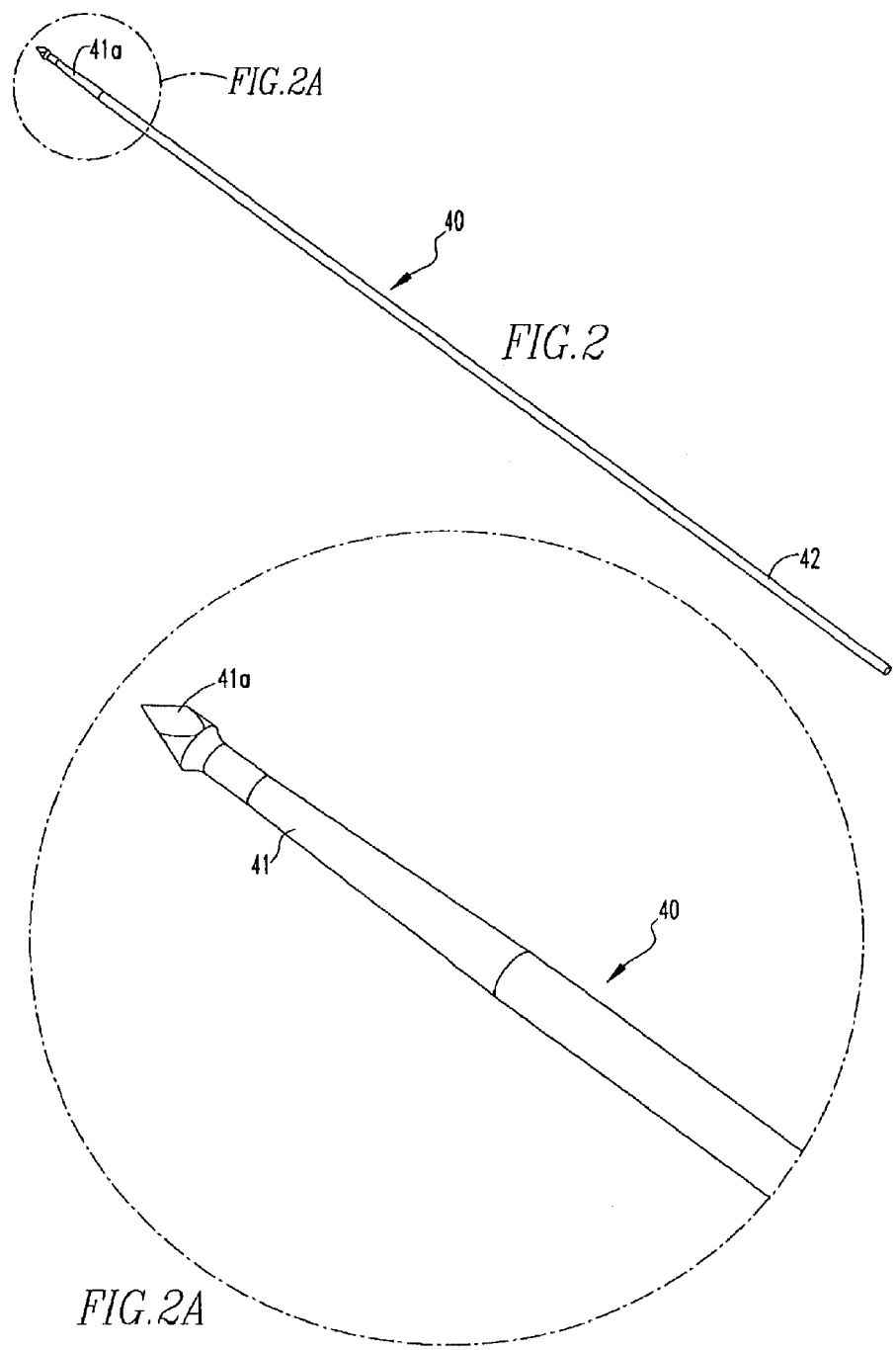
FIG. 2 shows the guide wire of the present disclosure.

After positioning the shaft 51 against the femur 20, the guide wire 40 is then inserted through the shaft 51. As shown in FIGS. 2 and 2A, the guide wire 40 includes a first end 41 having a pointed tip 41a and a second end 42. The second end 42 is coupled to a drill (not shown) and the drill is operated to insert the guide wire 40 through the femur 20. The guide wire 40 includes a flexible metal material, such as nitinol or other flexible metal material, which allows the first end 41 of the wire 40 to bend along the curved distal end 51a of the shaft 50 and be inserted into the femur 20 along the desired tunnel path.

Figure 3:
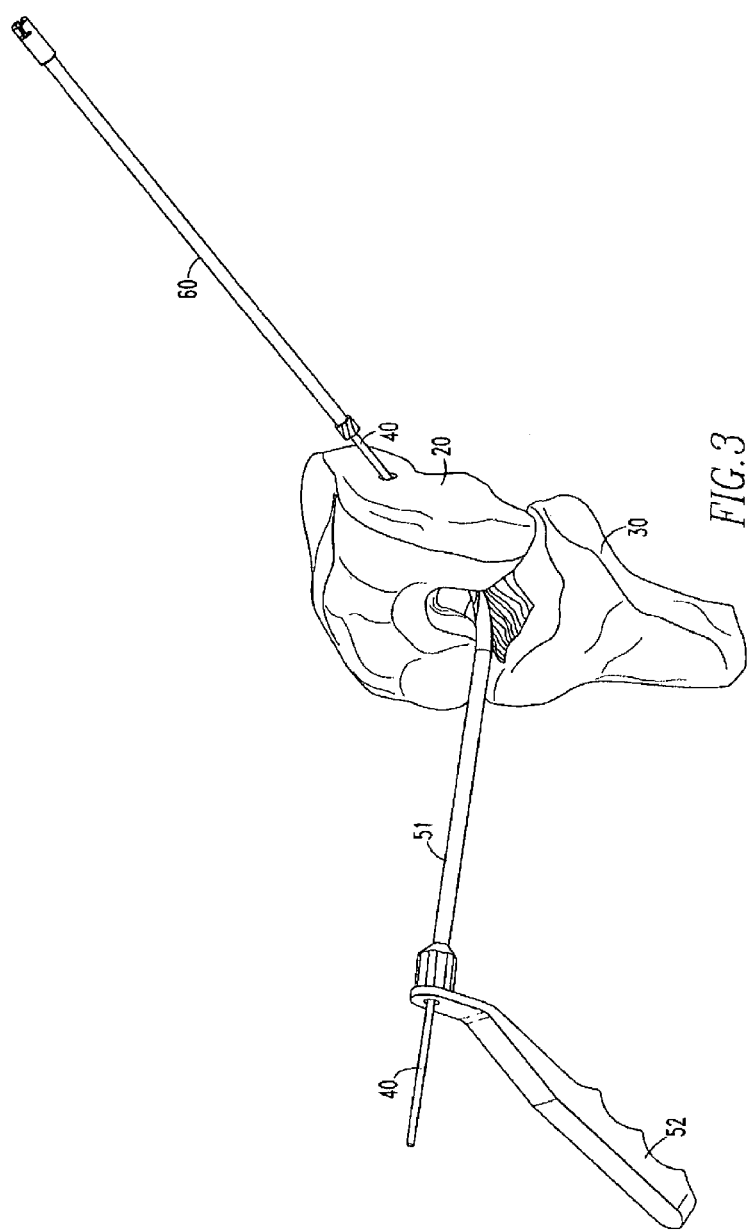
FIG. 3 shows placement of a drill mechanism of the present disclosure over the first end portion of the guide wire of the present disclosure.
Figure 4:
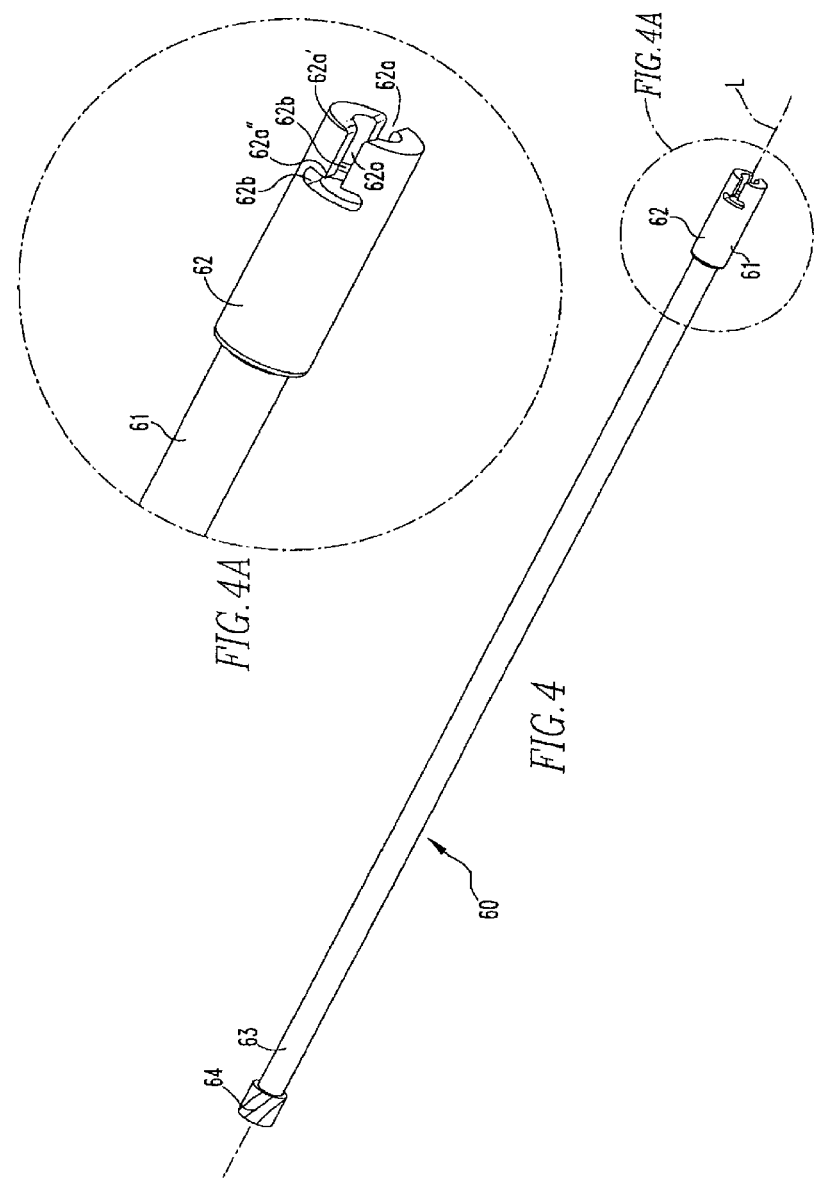
FIG. 4 shows the drill mechanism of the present disclosure.

Once the first end 41 of the wire 40 has been inserted through the femur 20, a cannulated drill mechanism 60 is positioned over the first end 41, as shown in FIG. 3. The drill mechanism 60, as shown in FIGS. 4 and 4A, includes a first end 61 having an attachment portion 62 and a second end 63 having a drill bit 64. The attachment portion 62 includes a first set of slots 62a, wherein the slots 62a are positioned on opposite sides of the portion 62 and extend parallel with a longitudinal axis L of the mechanism 60. Each of the slots 62a includes a first end 62a' and a second end 62a". A second set of slots 62b are located at the second end 62a" of the first set of slots 62a. The second set of slots 62b extends perpendicular to the first set of slots 62a. The purpose of the slots 62a,62b will be further described below. For the purposes of this disclosure, the drill bit 64 is 4.5 mm in diameter. However, the size of the drill bit 64 may vary based on surgeon preference and the size of the femoral tunnel.

Figure 5:
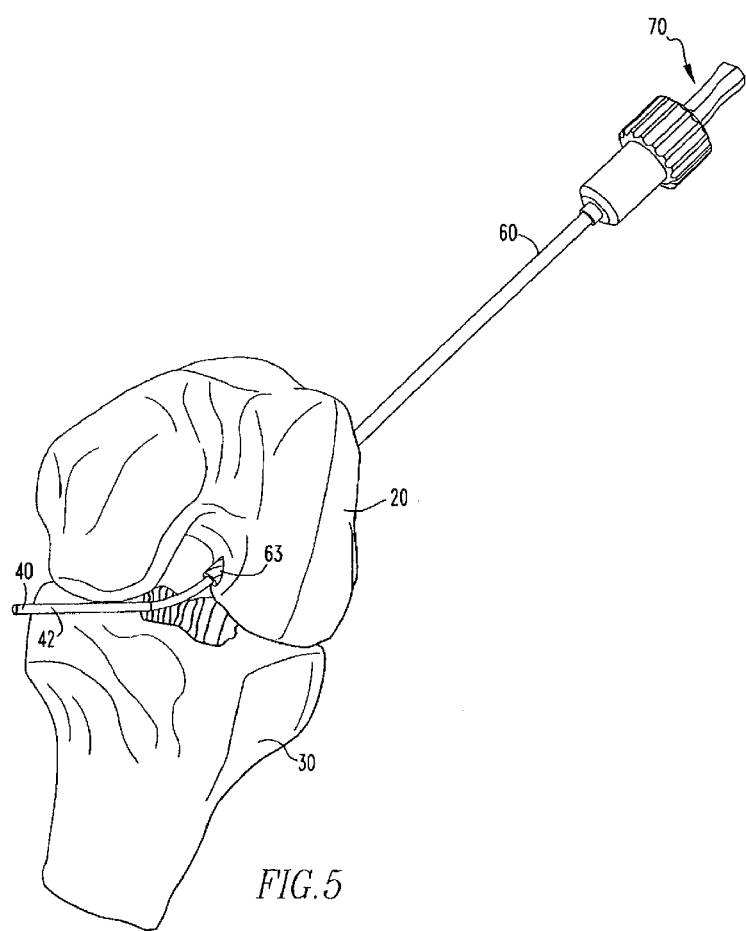
FIG. 5 shows creation of a bone tunnel through the femur using the drill mechanism of FIG. 4.
Figure 6:
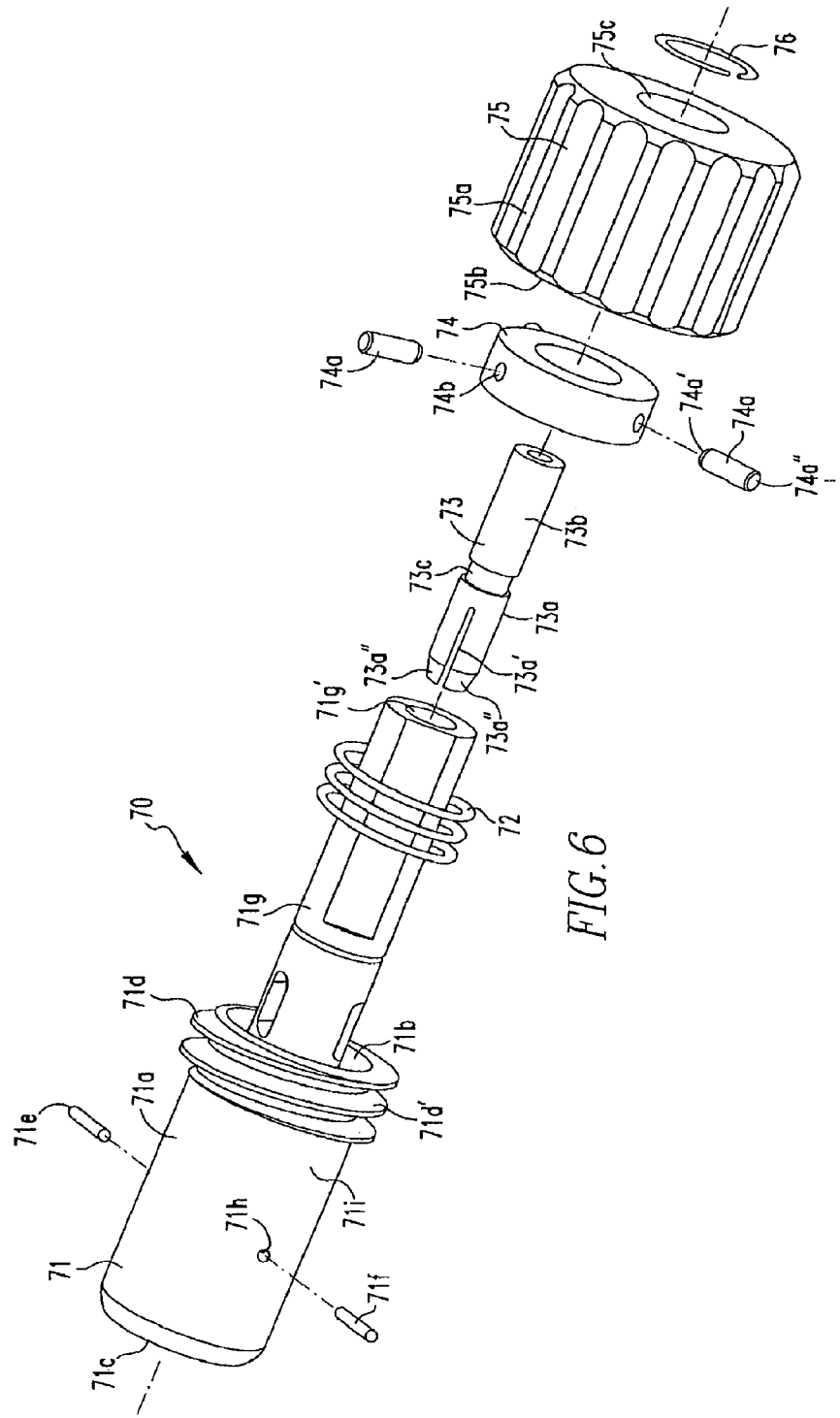
FIG. 6 shows an exploded view of the adaptor assembly of the present disclosure.

As shown in FIG. 5, after the mechanism 60 is positioned over the first end 41 of the wire 40, an adaptor assembly 70 is coupled to the mechanism 60 and the wire 40. The adaptor assembly 70, as shown in FIG. 6, includes an adaptor 71 having an outer surface 71a, an inner surface 71b, a wall 71h located between the inner and outer surfaces 71a,71b, a first end 71c, a second end 71d having threads 71d', a first pin 71e disposed through the wall 71h of the adaptor 71 and a second pin 71f disposed through the wall 71h opposite the first pin 71e, and a cannulated shaft 71g coupled to the inner surface 71b of the adaptor 71. A coiled spring 72 is disposed on the shaft 71g of the adaptor 71 and a ring 73 is disposed within the cavity 71g' of the shaft 71g. The ring 73 includes a first portion 73a having channels 73a' that divide the first portion into sections 73a", a second portion 73b, and an annular depression 73c located between the first and second portions 73a,73b.

Figure 7A:
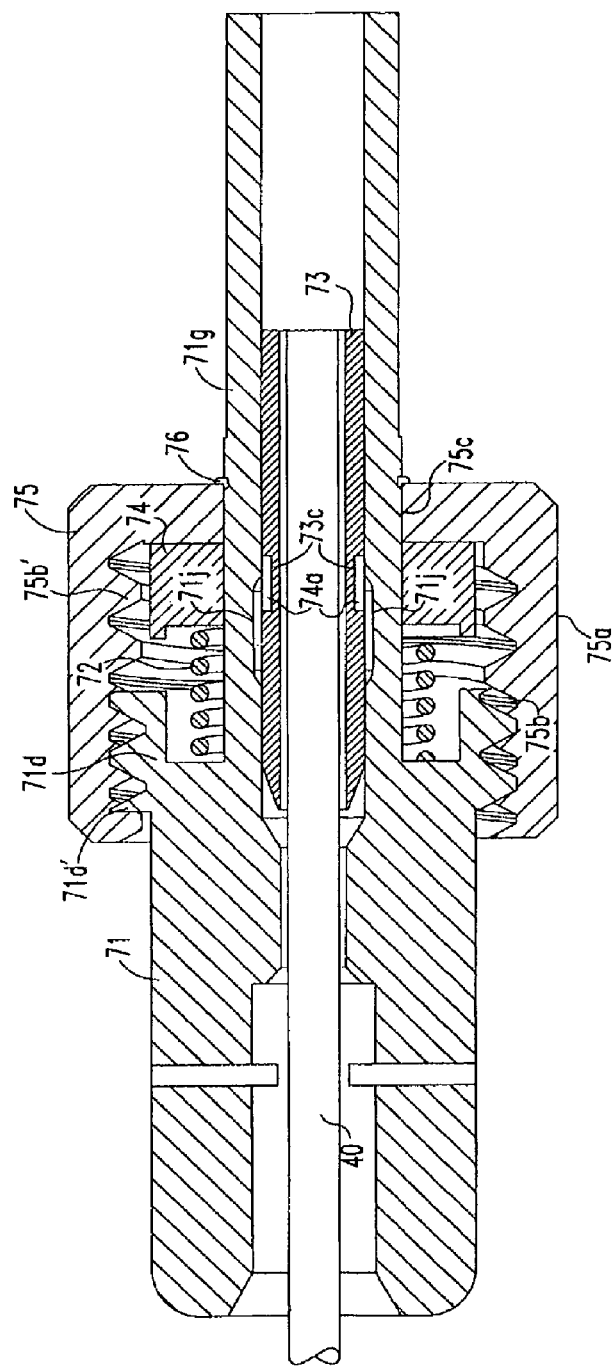
FIG. 7A shows a cross-sectional view of the adaptor assembly of the present disclosure.
Figure 7B:
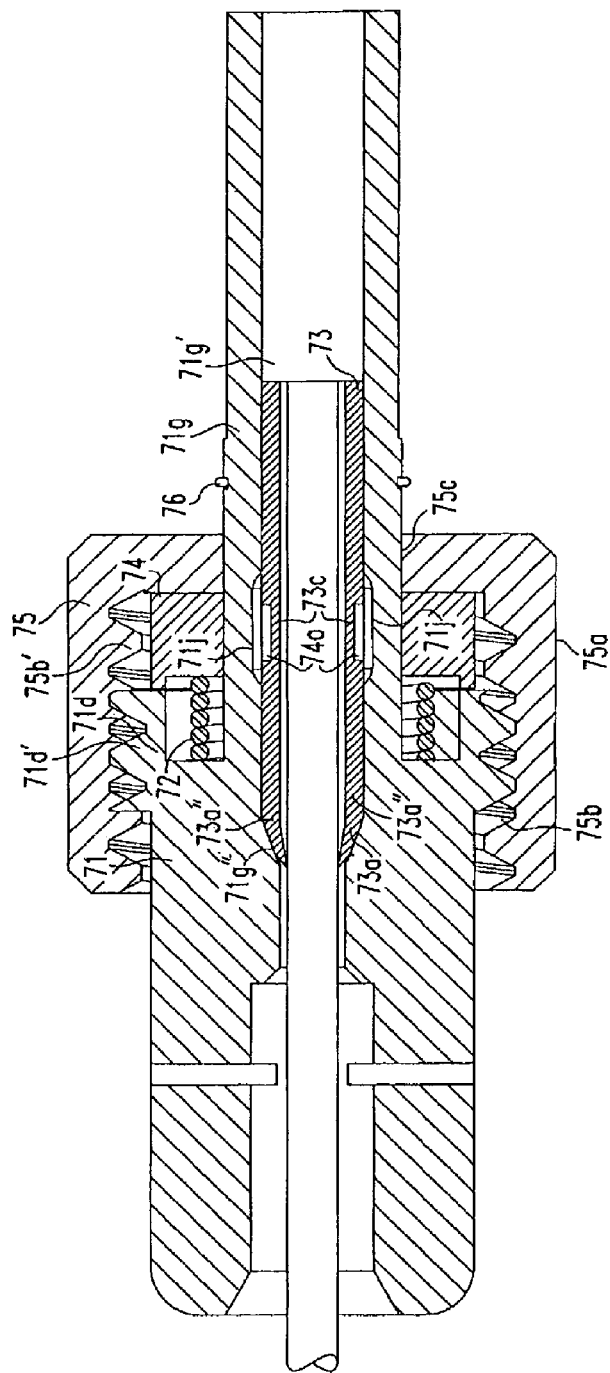
FIG. 7B shows another cross-sectional view of the adaptor assembly of the present disclosure.

As shown in FIGS. 6, 7A, and 7B, a collar 74 is coupled to the shaft 71g and ring 73 via screws 74a that extend through openings 74b in the collar 74, through the openings 71j, and into the annular depression 73c. Each screw 74a has a first end 74a' that abuts the annular depression 73c of the ring 73 and a second end 74a". A nut 75 is coupled to the second end 71d of the adaptor 71 and covers the coiled spring 72, the ring 73, and the collar 74. The nut 75 includes an outer surface 75a, an inner surface 75b having threads 75b', and an opening 75c. A retaining ring 76 is located on the shaft 71g behind the opening 75c. The nut 75 is coupled to the second end 71d of the adaptor 71 via engagement between the threads 71d',75b' of the adaptor 71 and the inner surface 75b of the nut 75.

The adaptor assembly 70 is disposed on the attachment portion 62 of the mechanism 60 such that the first pin 71e and the second pin 71f are inserted into the first set of slots 62a. The adaptor assembly 70 is then rotated to insert the pins 71e,71f within the second set of slots 62b and thereby couple the adaptor assembly 70 to the mechanism 60. At the same time that the adaptor assembly 70 is disposed on the attachment portion 62, the shaft 71g and ring 73 are disposed over the guide wire 40, as shown in FIG. 7A. Upon rotation of the nut 75, the inner surface 75b of the nut 75 abuts the collar 74 and causes the collar 74 to move longitudinally, thereby causing the ring 73 to move longitudinally with the nut 75. As is shown in FIG. 7B, during continued rotation of the nut 75, the first portion 73a of the ring 73 engages a beveled portion 71g" of the cavity 71g', and causes the sections 73a" of the first portion 73a to be reduced and engage the guide wire 40, thereby locking the adaptor assembly 70 to the guide wire 40. The spring 72 maintains tension on the collar 74 and, as shown in FIG. 7B, is compressed as the collar 74 moves longitudinally.

Figure 8:
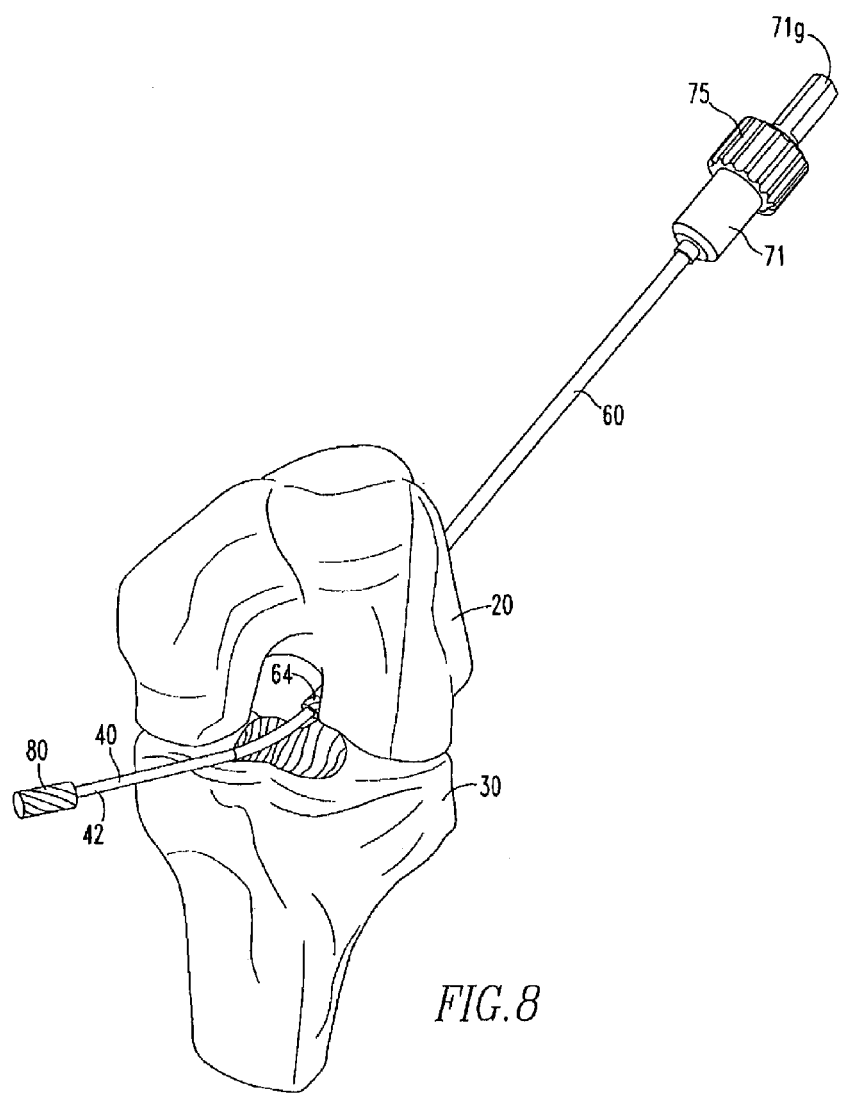
FIG. 8 shows attachment of a drill bit assembly of the present disclosure to the guide wire of FIG. 2.
Figure 9A:
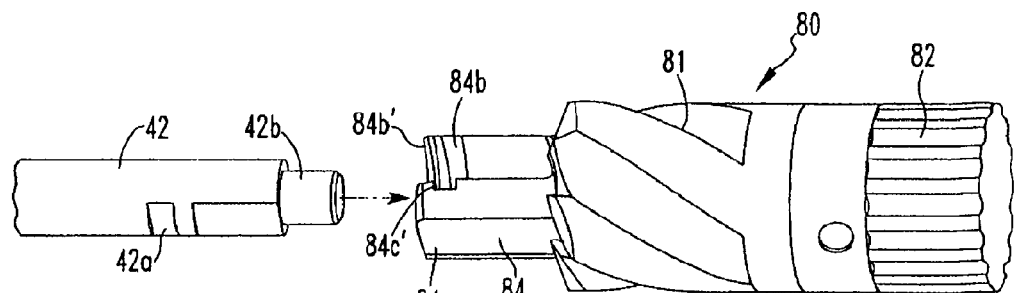
FIG. 9A shows the second end portion of the guide wire of FIG. 2 and the drill bit assembly of FIG. 8.
Figure 10:
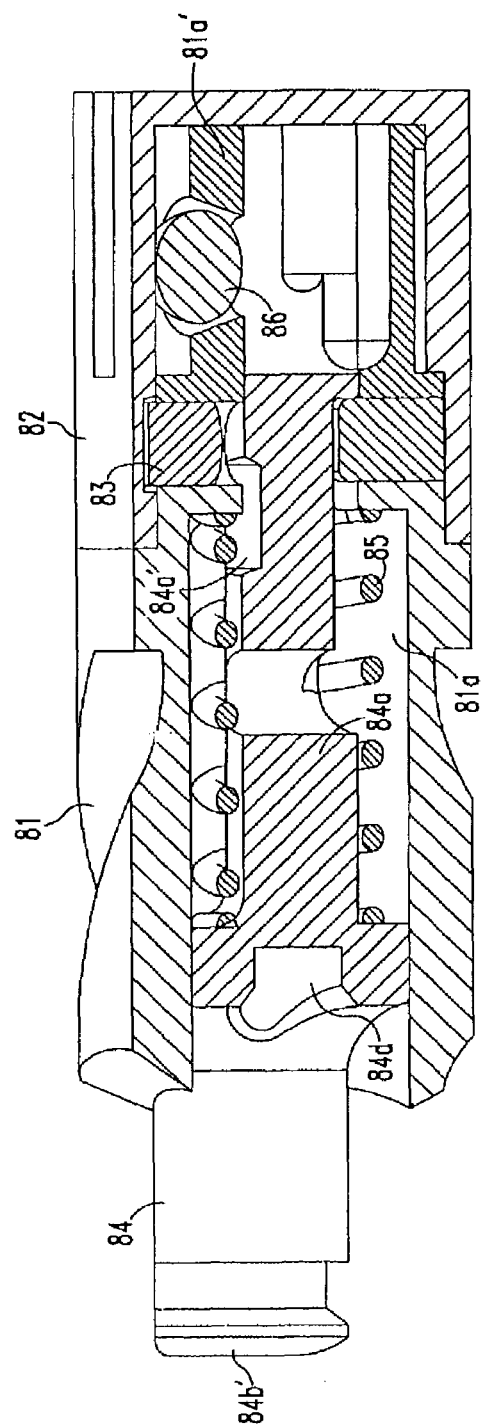
FIG. 10 shows a cross-sectional view of the drill bit assembly of FIG. 8.

After the adapter assembly 70 is coupled to the mechanism 60 and wire 40, a drill is coupled to the shaft 71g and operated to create a tunnel within the femur 20. Once the drill bit 64 exits the femur 20 and the tunnel is created, operation of the drill is discontinued. As shown in FIG. 5, the second end 42 of the guide wire 40 is extended from the second end 63 of the mechanism 60 by rotating the nut 75 to disengage the ring 73 from the guide wire 40 and pulling on the second end 42 of the guide wire 40. As shown in FIG. 8, a drill bit assembly 80 is then coupled to the second end 42 of the guide wire 40. The drill bit assembly 80, as shown in FIGS. 9A and 10, includes a housing 81 and a knob 82 coupled to the housing 81 via a pin 83. The housing 81 includes an inner cavity 81a. Disposed within the cavity 81a is a locking mechanism 84. The locking mechanism 84 includes a shaft 84a, a first 84b and second 84c finger coupled to the shaft 84a, and a detent 84d located between the fingers 84b,84c and the shaft 84a. A spring 85 is disposed around the shaft 84a. The shaft 84a includes a dimple 84a' and each finger 84b,84c includes a rim 84b',84c'. The surface 81a' of the inner cavity 81a includes a detent ball 86.

Figure 9B:
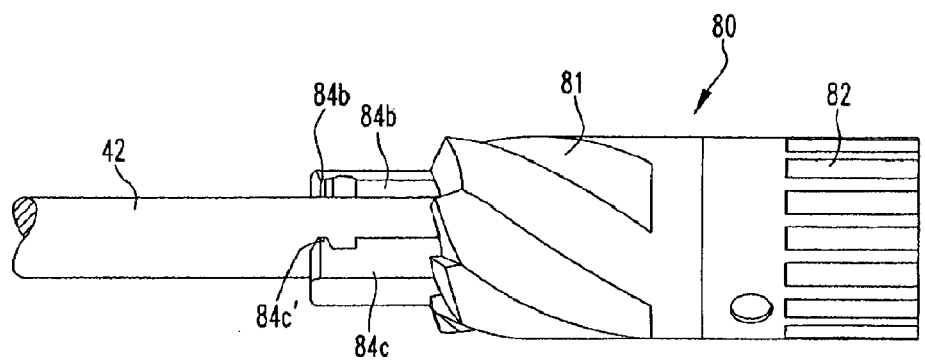
FIG. 9B shows coupling of the second end portion of the guide wire to the drill bit assembly.
Figure 9C:
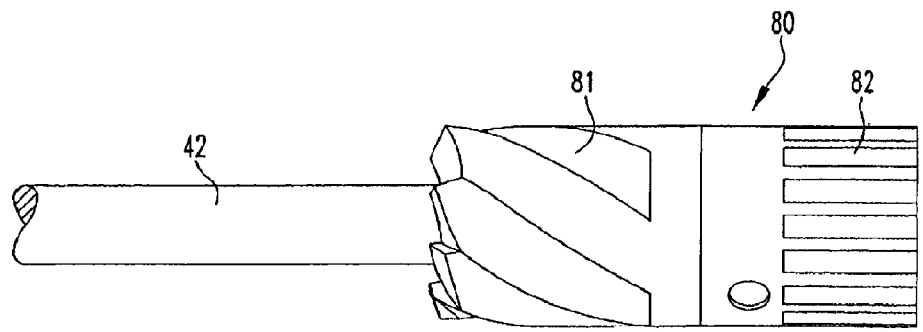
FIG. 9C shows placement of the second end portion of the guide wire within the drill bit assembly.

As shown in FIGS. 9A and 9B, the second end 42 of the guide wire 40 includes grooves 42a and a tip 42b. For the purposes of FIG. 9A, only one groove 42a is shown. However, a second groove is present opposite the groove 42a shown in FIG. 9A. The drill bit assembly 80 is coupled to the second end 42 such that the tip 42b is disposed within the detent 84d and the rims 84b',84c' are disposed within the grooves 42a. After coupling of the drill bit assembly 80 to the second end 42, the second end 42 and locking mechanism 84 are pushed into the inner cavity 81a of the housing 81 such that the spring 85 is compressed and the knob 82 is then rotated to dispose the detent ball 86 within the dimple 84a', thereby fixating the drill bit assembly 80 to the guide wire 40, as shown in FIGS. 9B & 9C.

Figure 11:
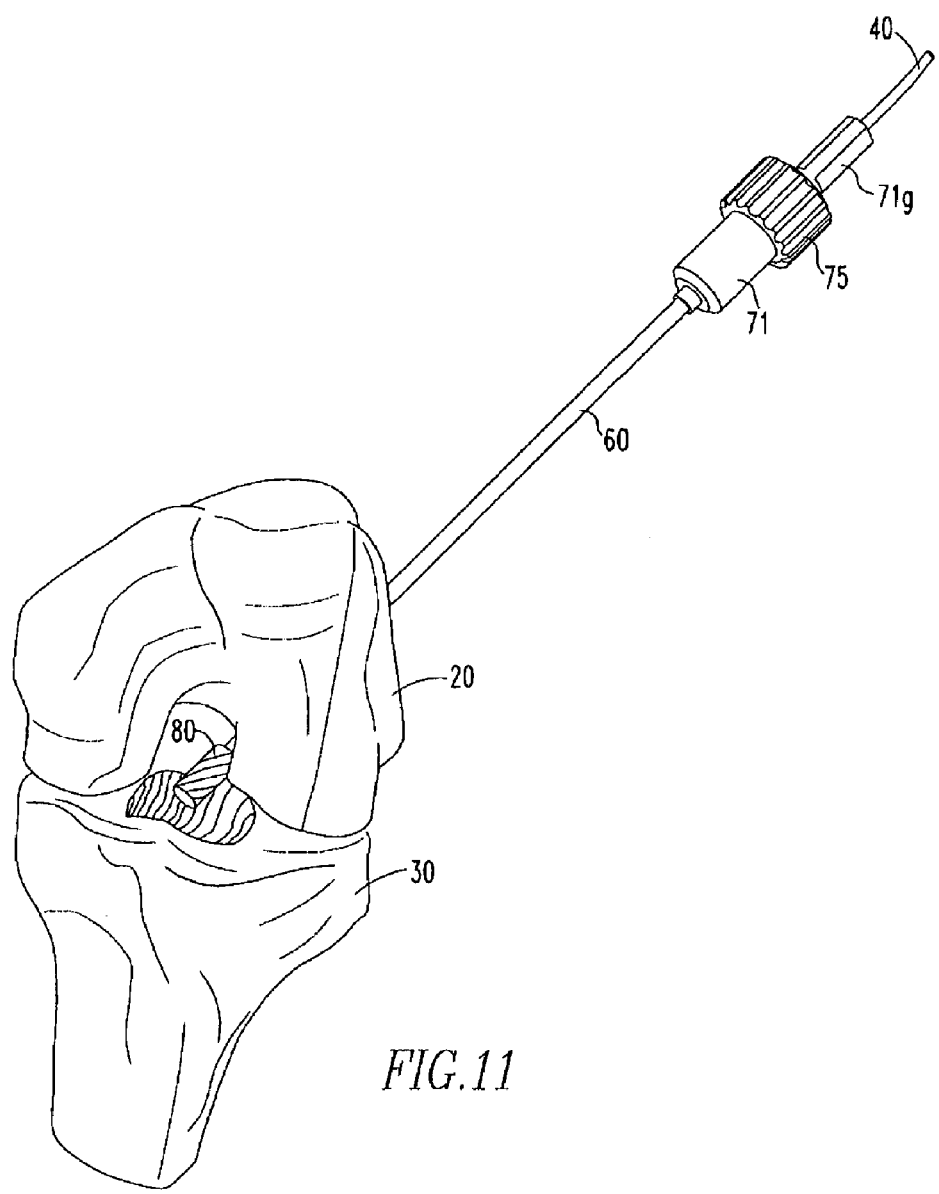
FIG. 11 shows the drill bit assembly of FIG. 8 abutting the drill bit of the drill mechanism of FIG. 4.
Figure 12:
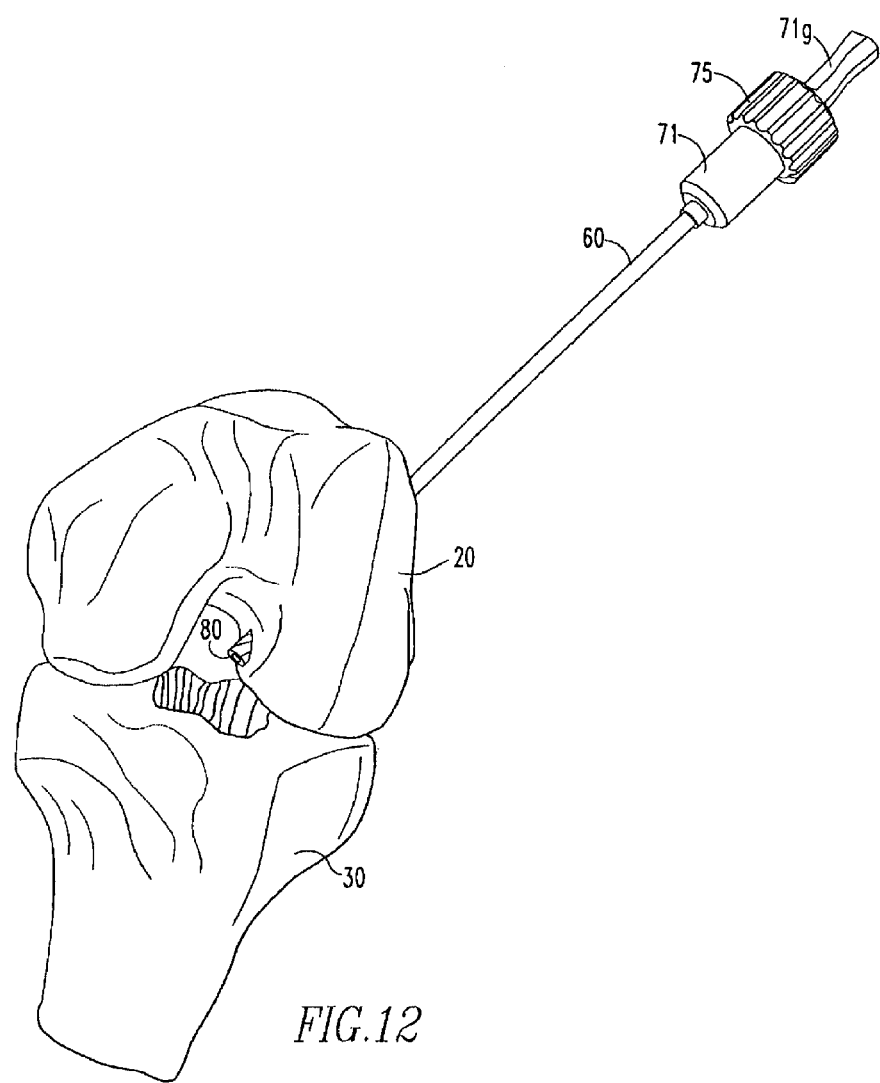
FIG. 12 shows creation of a counter bore in the femoral bone tunnel using the drill bit assembly.
Figure 13:
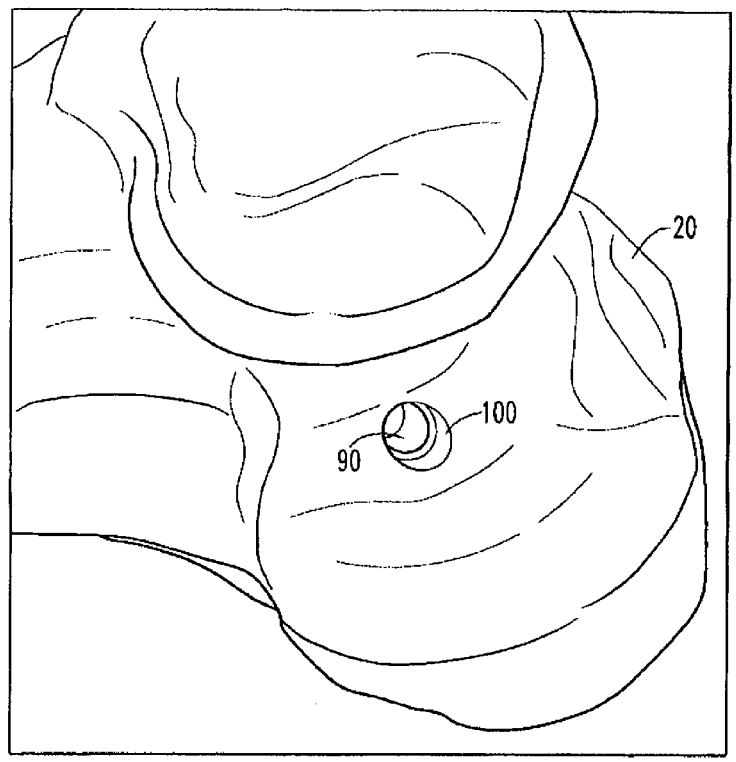
FIG. 13 shows the femoral bone tunnel and the counter bore.

As shown in FIG. 11, after coupling of the drill bit assembly 80 to the guide wire 40, the wire 40 is inserted back into the mechanism 60 until the drill bit assembly 80 abuts the drill bit 64 of the drill mechanism 60. The nut 75 is rotated until the ring 73 engages the wire 40 and locks the adaptor assembly 70 to the wire 40. A drill is then coupled to the shaft 71g and, upon operation of the drill, the mechanism 60, and thereby the drill bit assembly 80 is rotated to drill a certain depth and create a counter bore 100 along the tunnel 90, as is shown in FIGS. 12 & 13. The depth will vary based on surgeon preference and the size of the tissue graft. Having two areas of different diameter allows the tissue graft to remain in the larger area, i.e. the counter bore 100, and substantially reduces the possibility of the tissue graft extending out of the smaller area, i.e. the tunnel 90, due to the smaller size.

For the purposes of this disclosure, the drill bit assembly 80 has a diameter of 6 mm. However, the diameter may vary based on surgeon preference and desired size of the counter bore 100. The drill guide 50, drill mechanism 60, adaptor assembly 70, anchor assembly 80, and their components are made from biocompatible metal or non-metal material, such as stainless steel, titanium alloy, polymer, or other material, and may be made via a variety of molding and/or machining process known to those of ordinary skill in the art. In addition, while not shown in the figures, it is within the scope of this disclosure that the first end portion 41 of the guide wire 40, when inserted through the femur 20, is also inserted through the patient's skin.

As various modifications could be made to the exemplary embodiments, as described above with reference to the corresponding illustrations, without departing from the scope of the disclosure, it is intended that all matter contained in the foregoing description and shown in the accompanying drawings shall be interpreted as illustrative rather than limiting. Thus, the breadth and scope of the present disclosure should not be limited by any of the above-described exemplary embodiments, but should be defined only in accordance with the following claims appended hereto and their equivalents.

What is claimed is:

1. A cannulated drill mechanism comprising:
a tubular body comprising a first end and a second end;
a drill bit at the second end of the tubular body;
an attachment portion at the first end of the tubular body, the attachment portion including:
a first set of slots positioned on opposite sides of the attachment portion and extending parallel with a longitudinal axis of the mechanism, each of the first set of slots including a first end and a second end; and
a second set of slots located at the second ends of the first set of slots, the second set of slots extending perpendicular to the first set of slots;
wherein the second ends of the first set of slots intersect the second set of slots at an approximate midpoint of the second set of slots; and
an adaptor assembly disposed on the attachment portion of the tubular body, the adapter assembly including a housing and a shaft coupled to the housing, and a ring disposed within the shaft.

2. The mechanism of claim 1 wherein the drill bit is sized to match a size of a femoral bone tunnel.

3. The mechanism of claim 1 wherein the drill bit is 4.5 millimeters (mm) in diameter.

4. The mechanism of claim 1 wherein the adapter assembly further comprises:
a collar coupled to the shaft and the ring; and
a nut coupled to the housing of the adaptor, the nut including an opening through which the shaft is disposed.

5. The mechanism of claim 1 wherein the housing comprises a wall, a first pin disposed through the wall, and a second pin disposed through the wall opposite the first pin, and wherein the first pin and the second pin are housed within the first and second sets of slots.

6. The mechanism of claim 4 wherein an end of the housing comprises threads, and wherein the nut is coupled to the housing via engagement between the threads of the housing and threads in the opening of the nut.

7. The mechanism of claim 4 further comprising a coiled spring disposed on the shaft of the adaptor assembly, and wherein the nut covers the coiled spring.

8. The mechanism of claim 4 wherein the ring includes a first portion having channels that divide the first portion into sections, a second portion, and an annular depression located between the first and second portions; and wherein the collar is coupled to the shaft and the ring via screws extending through openings in the collar and into the annular depression of the ring.

* * * * *